US00PP08921P

United States Patent [19]

Davidson

[11] Patent Number: Plant 8,921

[45] Date of Patent: Oct. 4, 1994

[54] HYBRID TEA ROSE PLANT NAMED HARDRUBY

[76] Inventor: Harvey D. Davidson, #3 El Verano Rd., Orinda, Calif. 94563

[21] Appl. No.: 136,160

[22] Filed: Oct. 15, 1993

[51] Int. Cl.[5] ..... A01H 5/00

[52] U.S. Cl. ..... Plt./20

[58] Field of Search ..... Plt. 11, 20, 19, 21

*Primary Examiner*—Howard J. Locker

[57] ABSTRACT

A new rose variety of the Hybrid Tea class characterized by having large well formed red flowers on a bush with extremely glossy foliage and excellent disease resistance.

1 Drawing Sheet

The present invention relates to a new and distinctive variety of rose plant of the Hybrid Tea class, which was originated by my crossing 'Pink Favorite' (U.S. Plant Pat. No. 1,523) as the seed parent with 'Simon Bolivar' (U.S. Plant Pat. No. 2,705) as the pollen parent.

Among the novel characteristics possessed by the new variety which distinguish it from its:

(a) Parents and all other varieties of which I am aware are:
  (1) A plant which has foliage of remarkably high gloss;
  (2) A large red flower showing magenta hues with aging; and
  (3) A vigorous plant of medium height.

(b)
  *Seed parent.*—Pink flowers; tall.
  *Pollen parent.*—Orange/red flowers; matte foliage.

Asexual reproduction of the new rose variety by budding, as performed at Tulare, Calif. shows that the aforementioned and all other distinctive characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in the color description herein refers to plate numbers in the aforementioned color chart, e.g. "53A" is plate "53A" of The Royal Horticultural Society Colour Chart.

Parentage:
  *Seed parent.*—Pink Favorite'.
  *Pollen parent.*—'Simon Bolivar'.
Class: Hybrid Tea.

The following observations are made of specimens grown outdoors in Contra Costa County, Calif., in the month of September.

FLOWER

Blooming Habit

A. Bud:

(1) Size.—Fully mature, sepals enclosed, 22–25 mm from base of sepals.
(2) *Form.*—Ovoid.
(3) *Sepals.*—27 to 30 mm in length; 6–8 mm extension beyond bud; no serration shown on sepal edges. Generally 3 out of 5 sepals show appendages on each side, 2 to 5 mm length; heavy cotton matting on inner surface of sepals. Smooth on outer surface. Glandular development on sepal edgs. Outside color — 145A; inside — 145C.
(4) *Peduncle.*—Length —9 to 10 cm; Surface — smooth, no prickles, a few glandular hairs. Strength — stiff, slight curvature. Color — 146A.
(5) *Receptacle.*—Shape — rounded, 12 mm. Color — 146d, touch of 180C.
(6) *Color.*—When sepals first divide, outside petals — close to 61B, immediate opening inside petals close to 61C.

B. Bloom:
(1) *Size.*—Average when open — 12 to 14 cm.
(2) *Borne.*—Single.
(3) *Form.*—Globular; Opens in loose manner.
(4) *Petalage.*—Average number — 24 to 30.
(5) *Color.*—Early open 61C inside; 61B outside. Fully open 57C inside; 61B outside. Base of each petal 14C.

C. Petals:
(1) *Texture.*—Moderate.
(2) *Appearance.*—Flexed; satiny.
(3) *Form.*—Rounded, base to top edge: 6 cm; Horizontal center: 6 cm.
(4) *Arrangement.*—Loose, somewhat irregular.
(5) *Petaloids in center.*—Average 2 to 3.
(6) *Persistence.*—Drop off cleanly.
(7) *Fragrance.*—Strong.
(8) *Lasting quality.*—On plant 5–6 days; Cut 3–4 days.

REPRODUCTIVE ORGANS

A. Stamen:
(1) *Arrangement.*—Regularly arranged around styles.
(2) *Number.*—Average 180 to 190.
(3) *Length.*—Average — 10 to 15 mm.
(4) *Filaments.*—Color — Close to 47C.
(5) *Anthers.*—Color — 23C.
(6) *Pollen.*—23B.

B. Pistil:

(1) *Styles.*—4 to 8 mm length; number 85 to 90; covered with fine white hairs; color: near 47A.

(2) *Stigma.*—Color — close to 155A.

(3) *Ovary.*—9 mm through center.

C. Hips:

*Mature.*—(1) Size 20–25 mm. (2) Color: 43D with shadings of 43B.

PLANT

A. Form: Moderately spread. Stems frequently curved upright.

B. Growth: Vigorous.

*Medium height.*—Average 70–90 cm.

C. Stem legnth:

*Basal break to flower bud tip.*—Average — 45 cm.

D. Foliage: Compound of 3 to 5 leaflets on bloom stem; 5 to 7 leaflets on main cains.

(1) *Mature size, 5 leaflet.*—Tip of terminal leaflet to stipule base 16–17 cm.

(2) *Quantity.*—Stem well covered.

(3) *Color.*—New foliage upper side 146A; under side 146C. Old foliage upper side 137A; under side 137C, veining 178B.

(4) *Shape.*—Oval with center pointed.

(5) *Texture.*—Firm, very leathery, remarkably high gloss.

(6) *Edge.*—Fine serration on outer edge. Average 6 points per 1 cm, with up to 1 mm peak.

(7) *Rachis.*—Slight glandular hair on upper side; lower side: 6 to 7 hooked prickles 2 mm length, spaced near to 1 cm apart.

(8) *Stipules.*—Length 2 cm; auricle to 7 mm. Edge of stipule to tip of auricle with many glandular hairs.

D. Resistance to diesase:

*Mildew, rust.*—excellent.

*Blackspot.*—Good.

E. Wood:

*New wood.*—Color 144A. Bark — smooth.

*Old wood.*—Color 138A. Bark — smooth.

F. Thorns:

(1) *Shape.*—Slight downward curvature.

(2) *Color.*—Near to 173C.

(3) *Spacing.*—Average 7–8 per 30 cm.

G. Winter hardiness: Very good.

I claim:

1. A new and distinct variety of rose plant of the Hybrid Tea class, substantially as herein shown and described.

* * * * *

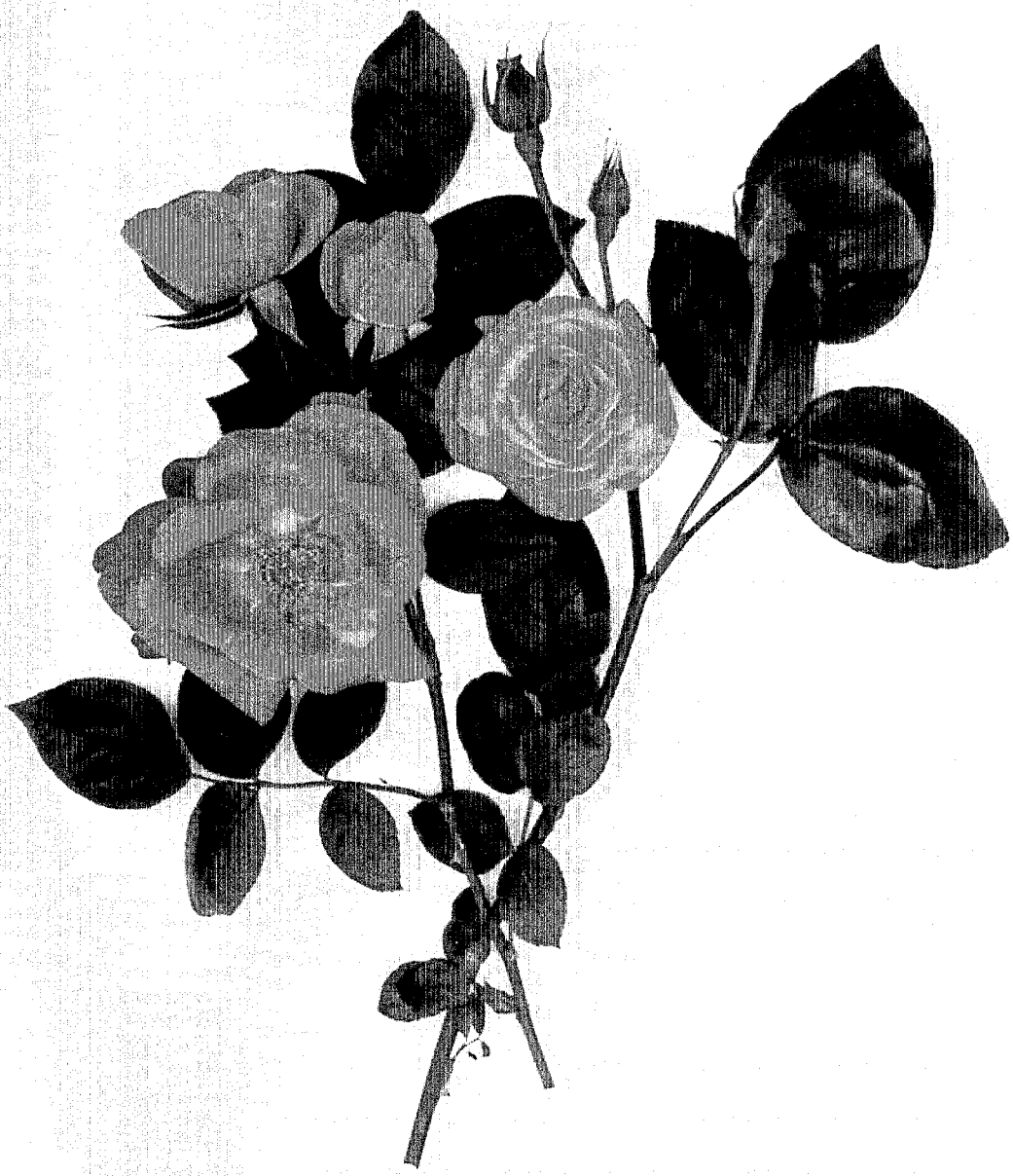

UNITED STATES PATENT AND TRADEMARK OFFICE

CERTIFICATE OF CORRECTION

PATENT NO. : PP 8,921

DATED : October 4, 1994

INVENTOR(S) : Harvey D. Davidson

It is certified that error appears in the above-indentified patent and that said Letters Patent is hereby corrected as shown below:

On the title page, item [54] change "HARDRUBY" to --HADRUBY--.

Signed and Sealed this

Twenty-first Day of March, 1995

*Attest:*

Bruce Lehman

BRUCE LEHMAN

*Attesting Officer*

*Commissioner of Patents and Trademarks*